United States Patent [19]

Sallee et al.

[11] Patent Number: 4,846,827

[45] Date of Patent: Jul. 11, 1989

[54] METHOD AND APPARATUS FOR APPLYING AN ARTICLE WHICH INCLUDES AN ELASTIC MEMBER COMPRISING HOT MELT PRESSURE SENSITIVE ADHESIVE APPLIED TO A HEAT SENSITIVE WEB

[75] Inventors: Lorry F. Sallee, Pine River; Russell E. Thorson, Appleton, both of Wis.

[73] Assignee: Kimberly-Clark Corporation, Neenah, Wis.

[21] Appl. No.: 234,878

[22] Filed: Aug. 18, 1988

Related U.S. Application Data

[60] Division of Ser. No. 13,995, Apr. 14, 1987, Pat. No. 4,801,985, which is a continuation of Ser. No. 840,269, Mar. 17, 1986, abandoned, which is a division of Ser. No. 697,315, Feb. 1, 1985, Pat. No. 4,610,745.

[51] Int. Cl.⁴ .......................................... A61F 13/16
[52] U.S. Cl. .............................. 604/385.2; 604/371
[58] Field of Search ........................ 604/385.2, 371

[56] References Cited

U.S. PATENT DOCUMENTS

| | | | |
|---|---|---|---|
| 3,245,407 | 4/1966 | Mason | 128/284 |
| 3,639,917 | 2/1972 | Althouse | 2/270 |
| 3,912,565 | 10/1975 | Koch et al. | 156/85 |
| 4,287,013 | 9/1981 | Running | 428/354 |
| 4,300,967 | 11/1981 | Sigl | 156/164 |
| 4,339,483 | 7/1982 | Ueno et al. | 428/35 |
| 4,366,814 | 1/1983 | Riedel | 128/156 |
| 4,393,106 | 7/1983 | Marahashi et al. | 156/229 |
| 4,411,954 | 10/1983 | Butch, III et al. | 428/343 |
| 4,417,935 | 11/1983 | Spencer | 156/80 |
| 4,418,123 | 11/1983 | Bunnelle et al. | 428/517 |
| 4,526,577 | 7/1985 | Schmidt et al. | 604/366 |
| 4,636,207 | 1/1987 | Buell | 604/385 A |
| 4,801,485 | 1/1989 | Sallee et al. | 428/198 |

Primary Examiner—C. Fred Rosenbaum
Assistant Examiner—Mark O. Polutta
Attorney, Agent, or Firm—Paul Yee

[57] ABSTRACT

The present invention provides a garment article which includes a body of gatherable material, and a heat sensitive, thermally-elasticizable ribbon material which is secured to the gatherable material with a hot melt adhesive. The hot melt adhesive is disposed on a surface of the thermally-elasticizable ribbon to provide a heat recoverable, elastomeric tape. The tape is adhesively secured to the garment by the hot melt adhesive, and is activated by an application of heat to shrink and shir the gatherable material.

16 Claims, 4 Drawing Sheets

METHOD AND APPARATUS FOR APPLYING AN ARTICLE WHICH INCLUDES AN ELASTIC MEMBER COMPRISING HOT MELT PRESSURE SENSITIVE ADHESIVE APPLIED TO A HEAT SENSITIVE WEB

This is a division of application Ser. No. 07/013,995 filed Apr. 14, 1987, now U.S. Pat. No. 4,801,485 which is a continuation of application Ser. No. 06/840,269 filed Mar. 17, 1986, now abandoned, which was a division of application Ser. No. 06/697,315 filed Feb. 1, 1985 and issued as U.S. Pat. No. 4,610,745 on Sept. 9, 1986.

TECHNICAL FIELD

This invention relates generally to methods and apparatus for applying hot melt adhesive to a heat sensitive web, for example, a heat shrinkable web for forming an elasticized body-encircling portion of a disposable garment.

BACKGROUND

Numerous articles are designed for single or temporary use and have become commercially important in recent years. These articles are meant to be disposed of after being used once instead of being laundered or cleaned for re-use. Examples of garments of this genereal type are disposable diapers; adult incontinence garments, disposable bedsheets; disposable shower caps; garments intended for single use in hospitals such as surgical gowns, surgical hats and booties; and single use or disposable pajamas and the like intended to be worn by patients in the hospital for a short stay. Articles other than garments are also within this class, such as protective covers, dust covers, etc. Single use or disposable articles of this type are made of lightweight film or sheet materials such as thermoplastic films, non-woven fabrics of various materials such as thermoplastic or cellulosic fibers, paper, coated film or paper, and various composites of one or more of these types of materials such as disposable diapers which include, for example, layers of polyethylene and polypropylene which sandwich an absorbent material or fluff. These garment materials are distinguishable from textiles used to make a sewn garment or article which is intended for long-term use and subject to repeated laundering or dry cleaning.

Disposable articles of the type under consideration are economically feasible only when they can be manufactured at high production rates using techniques typical of converting film materials, such as heat sealing, sonic sealing, adhesive bonding, etc., instead of the sewing techniques customary with textile garments meant for longterm use. Even with the disposable articles, however, it is often desirable to shir the article, i.e., form an elasticized portion in order to provide a snug fit. In the case of disposable garments intended to be worn by human beings, for example, it may be necessary to provide a gown or similar item with elasticized wrists, or to produce a disposable diaper with elasticized waist portions and leg portions in order to provide a snug fit, or to provide disposable booties with an elasticized ankle-encircling portion. In the case of other products such as bed sheets and dust covers, a marginal portion that can fit snugly about an article with which the product is used is often required.

Because articles of this type need to be made at high production speeds, the formation of an elasticized portion by sewing in a strip of elastic material as is common in the production of textile garments is not practical.

Among the methods that have been developed or proposed in the art to form elasticized portions of disposable products are several which involve the use of heat, such as: (1) constructing the article of an oriented thermoplastic film and contact heating selected portions thereof to cause them to heat shrink and form integral elastic portions (see U.S. Pat. No. 3,245,407); (2) applying to the article a type that is elastic at room temperature but rendered inelastic at elevated temperatures and heating selected portions of the tape to kill its elasticity (see U.S. Pat. No. 4,300,967 and published United Kingdom Patent Application No. 2,016,262); and (3) applying a tape of a material that is inelastic at room temperature but rendered elastic by the application of heat (see U.S. Pat. Nos. 3,639,917 and 3,912,565).

The method disclosure of U.S. Pat. No. 3,639,917 involves heating a garment section bearing heat recoverable elastomeric tape to temperatures in the range of 75° C. to 150° C. (167° F. to 302° F.) such as by use of a hot air gun, iron or an oven. U.S. Pat. No. 3,912,565 discloses forming an elasticized article by heating heat shrinkable uniaxially oriented polyurethane tape to a temperature slightly above its second order phase transition temperature, 100° C. (212° F.) being disclosed as an operable temperature; for this purpose, the patent states the heat may be applied by gas, such as hot air, or liquid.

In U.S. Pat. No. 3,912,565, the tape is disclosed as stretched by application of external heat, cooled at the stretched condition, then again heated by application of external heat to effect controlled heat shrinkage. In U.S. Pat. No. 3,639,917, block copolymers are irradiated, then expanded at elevated temperatures to achieve a new length, then cooled to maintain the copolymers at the new length. Subsequent reheating returns the copolymers to their original length.

Still other thermally-elasticizable materials, which include a preferred form useful in articles such as disposable diapers, can be oriented either by machine direction stretching or compression rolling to create potential elastic energy which can be recovered by heating to their activation temperature. Such materials, as are described in copending application Ser. No. 896,916 entitled "Heat-Shrinkable Elastomer", filed Apr. 8, 1986 (Attorney Docket Number 7325), a continuation-in-part of U.S. patent application Ser. No. 606,082 filed May 1, 1984 and entitled Heat Shrinkable Elastomer, Method of Producing the Elastomer and Articles Utilizing the Elastomer, attorney docket No. 6525, assigned to the assignee of this application, have activation temperatures from about 125° F. to about 230° F.

As described above, it is imperative that this type of article be manufactured at high production rates in order to make them economically feasible. In this regard, it is advantageous to utilize a pressure sensitive hot melt adhesive to secure the tape to the article or garment. Such molten hot melt adhesives are formed at temperatures of from 140° C. to about 190° C. (284° F. to about 374° F.). Since the activation temperatures of the thermally-elasticizable materials described above are below this range, and particularly the preferred form of heat recoverable elastomeric tape which has an activation temperature in the range of from about 125° F. to about 230° F., the molten hot melt adhesive can result in premature activation of the elastomeric tape which is undesirable.

DISCLOSURE OF THE INVENTION

As used herein, the term "bead" refers to a band or ribbon of adhesive material.

A new process in which pressure sensitive hot melt adhesive is applied to heat sensitive material is provided in which the hot melt adhesive is heated and extruded through an exit nozzle and deposited on a surface of a cooling transfer mechanism in a substantially continuous bead and is caused to cool substantially uniformly across its width. A substantially continuous web of heat sensitive material is brought into contact with the adhesive bead after it has cooled sufficiently to prevent adverse reaction with the heat sensitive material, e.g., to a temperature below the activation temperature of a heat shrinkable material, and is pressed into intimate contact with and bonded to the adhesive. Thereafter, the web and adhesive are stripped from the transfer mechanism.

Ideally, the cooling transfer mechanism has a flat surface and the formed head of adhesive is flat and rectangular in cross-section so that cooling occurs uniformly across its width. As a practical matter, some departure from a purely flat surface and a purely rectangular cross-section will occur and may even be desirable, and it is to be understood that the bead should have sufficient thickness across its width to enable sufficient cooling without retaining undesirable "hot spots" in the adhesive. The cooling transfer mechanism preferably is a rotating chill roll, although other structures may be used, and the web preferably is brought into contact with the adhesive bead before pressure is applied to intimately contact and bond the web and adhesive.

The bonded heat sensitive web and adhesive are adapted to be formed on a high production, continuous assembly and can be used to form heat recoverable elastomeric tape which can be attached to a disposable garment or the like. The hot melt adhesive provides instant bonding to the web, unlike cold adhesives which can require up to 30 minutes or more to bond. Since the adhesive has been cooled before application to the heat shrinkable web, the web is not prematurely activated. Thus, attendant process problems are avoided.

Also developed is an apparatus for practice of the method which includes means for heating and extruding a hot melt pressure sensitive adhesive through an exit nozzle, a cooling transfer mechanism having a surface disposed adjacent and spaced by a gap from the exit nozzle for receiving a substantially continuous bead of adhesive from the nozzle, the bead having a cross-section operable to promote uniform cooling across its width by the cooling transfer mechanism, means for feeding a web of heat sensitive material into contact with the transfer mechanism surface and adhesive bead, means for pressing the web against the adhesive bead and transfer mechanism surface, and means for stripping the web and adhesive from the transfer mechanism surface. Preferably, the transfer mechanism is a rotating chill roll and its surface is flat, and the exit nozzle is shaped and positioned relative to the transfer mechanism surface so that the adhesive bead formed on the surface is relatively flat. The exit nozzle is spaced from the roll surface by a gap approximately equal to the thickness of the adhesive bead deposited on the roll.

The web and adhesive bead can contact and be pressed into engagement substantially simultaneously, but preferably pressed engagement occurs after initial contact. The stripping means preferably comprises a peel-off roll and means is provided to cause the web and adhesive to wrap around the peel-off roll at least about 90° and preferably about 180°. The chill roll is coated with a ceramic impregnated with polytetrafluoroethylene.

Still further, the invention includes a disposable garment which comprises a body of material, a heat sensitive elastomer for shirring the body of material, and a hot melt adhesive securing the elastomer to the body of material. Preferably, the heat sensitive material is a thermally elasticizable material, and the adhesive comprises a base polymer and a tackifier resin which is extruded at a temperature of from about 280° F. to about 375° F. A preferred heat sensitive material is a co-extruded film having an inner layer of a polyether block amide resin consisting of linear regular chains of rigid polyamide segments and flexible polyether segments, and at least one outer layer of ethylene/vinyl acetate copolymer.

The method, apparatus and product of this invention provide new and useful results, as explained in the description which follows, which in part will be obvious from the description, or which may be learned by practice of the invention. The objects and advantages of the invention may be realized and attained by means of the instrumentalities and combinations particularly pointed out in the appended claims.

BEST MODES FOR CARRYING OUT THE INVENTION

The drawings depict the method, apparatus and product of this invention employed in applying a hot melt pressure sensitive adhesive to a web of heat shrinkable material used in the formation of shirred or elasticized waist portions of a disposable infant's diaper, which is a particularly useful application of the present invention. However, it should be borne in mind that this invention can be practiced advantageously with numerous other types of heat sensitive materials and adhesives, and is useful in applications to other types of articles so that the articles described herein are exemplary, and not limiting.

The detailed description is divided into four parts: (a) a background and product discussion; (b) a method description; (c) an apparatus description; and (d) a description of operational conditions.

(a) Background and Product

Figure 1:
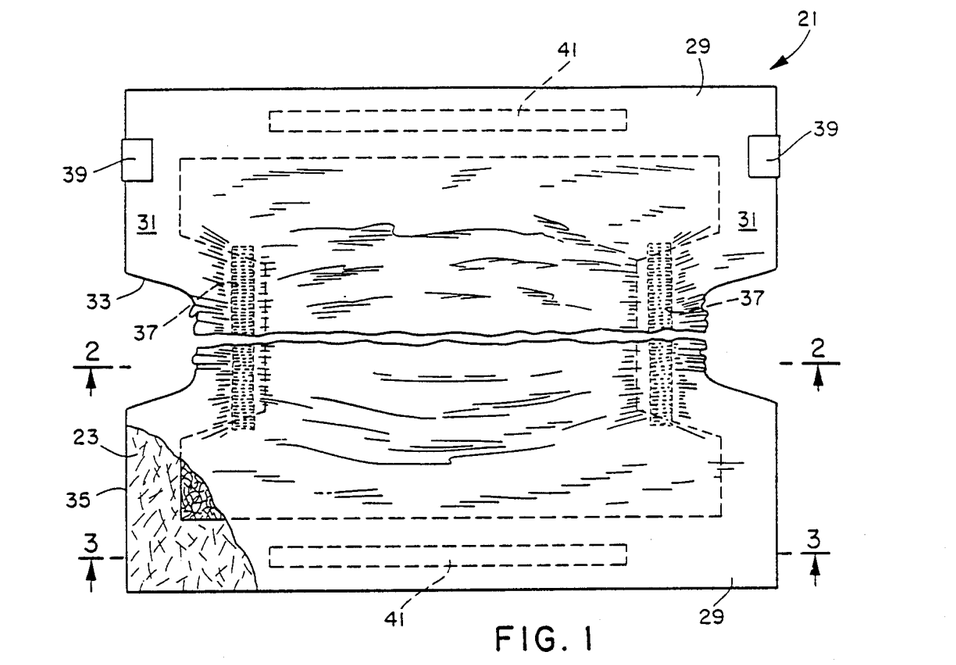
FIG. 1 is a plan view, with portions broken away, of an infant's disposable diaper as an example of a type of article with which the web and adhesive of this invention can be used and showing cut strips or ribbons thereof secured to the diaper and before heat shrinking.
Figure 2:
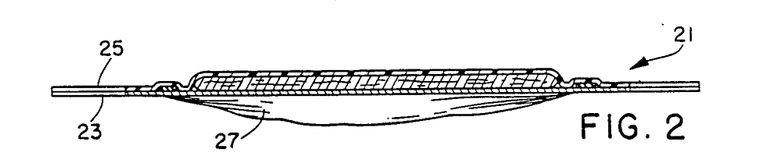
FIGS. 2 and 3 are sectional views of FIG. 1 along the plane of lines 2—2 and 3—3, respectively.
Figure 3:
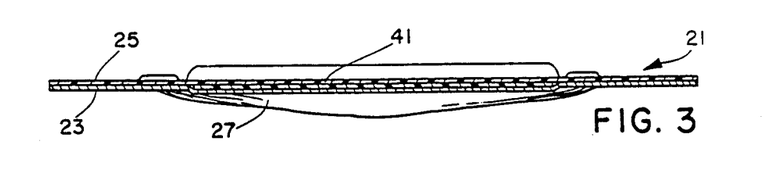
Figure 4:
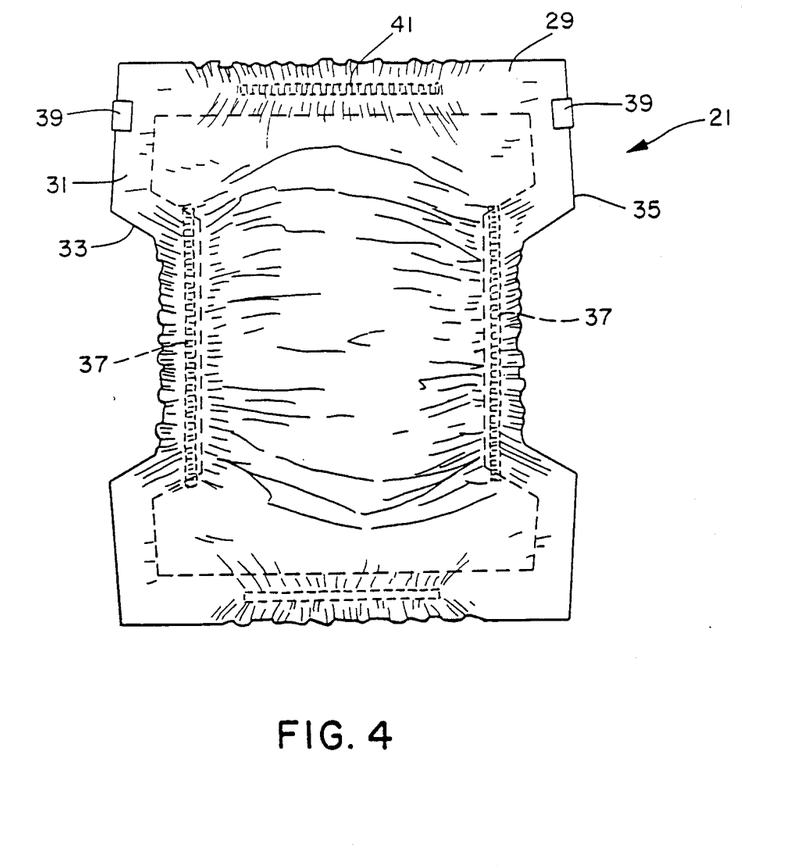
FIG. 4 is a plan view of the diaper of FIG. 1 after the ribbons are heat shrunk.

FIGS. 1, 2 and 3 illustrate a disposable diaper 21 comprising a liquid-permeable inner liner 23, a liquid-impermeable outer layer 25, and an absorbent batt 27 secured therebetween. The inner liner 23 and outer layer 25 are larger than the absorbent batt 27 and have end marginal portions 29 extending beyond the ends of the batt and side marginal portions 31 extending beyond the sides of the batt. The liner 23 and outer layer 25 are secured to each other along the marginal portions 29 and 31.

Conventional materials are used for these components of the diaper 21. The inner liner 23 may be any soft, flexible porous sheet which passes fluids therethrough and may comprise a non-woven web or sheet of polyolefin fibers such as polypropylene, wet strength tissue paper, a spun woven filament sheet, etc. It may be treated with a surfactent to aid in liquid transfer. The outer layer 25 is a liquid-impermeable layer and may comprise a thin web or sheet of plastic film such as polyethylene, polypropylene, polyvinylchloride or the like; it may be transparent or have an embossed or matt surface to be opaque. The absorbent batt 27 may be of any suitable material, generally cellulosic material such as an air-formed batt of wood pulp fibers commonly known as "fluff".

The inner liner 23, outer layer 25 and batt 27 may be combined with one another in any suitable manner to form the finished diaper. The elements may be bonded to one another by means of strips or patterns of hot melt or pressure sensitive adhesive, overall or pattern heat sealing, strips of double face pressure sensitive adhesive tape, etc. A particularly effective bonding system is the use of spaced parallel lines of hot melt adhesive on the interior surface of the outer layer 25, with the absorbent batt bonded to the layer 25 along sections of the lines of adhesive, and the inner layer 23 bonded to the layer 25 along other sections of the lines of adhesive within the marginal portions 29 and 31 outside the batt.

The diaper is of a generally hourglass or "I" shape including a central narrowed crotch section 33 and waistband sections 35 along each end thereof. Elongate elastic means 37 are secured in place adjacent the absorbent batt 27 on each side thereof to develop gathered elastic leg portions that are conformable with an infant's legs. Conventional pressure sensitive tapes 39 are attached to one waistband section 35.

In use, the diaper 21 is fitted to an infant with the inner layer 23 against the child's skin. One marginal portion 29 encircles part of the infant's waist and the other marginal portion 29 encircles the balance, with the two being overlapped and joined together by the pressure sensitive adhesive tapes 39 in order to hold the diaper in place.

The diaper 21 of FIGS. 1–3 includes thermally-elasticizable strips or ribbons 41 for shirring the diaper, which ribbons are secured to the interior surface of the outer layer 25, best seen in FIG. 3, there being one ribbon 41 positioned within each end marginal portion 29 spaced inwardly from the outer edge thereof. Alternatively, the ribbons 41 can be secured to the exterior surface of the outer layer 25, or the interior or exterior surface of the liner 27. The ribbons 41 have a selected width and selected length, about one-quarter inch to one inch wide being suitable for most articles, and the length is as long as required for the particular article to which the ribbons are applied. A ribbon 41 usually will be a relatively thin, approximately 0.75 to 3 mils being suitable in most instances.

The thermally-elasticizable ribbon 41 is secured to the liner 23 or outer layer 25 most usefully by hot melt pressure sensitive adhesive disposed on the surface of the ribbon 41 which is to contact the inner liner or outer layer. The pressure sensitive adhesive is physically disposed on the ribbon surface in the form of one or more spaced parallel lines or beads extending longitudinally of the ribbon 41. Desirably, the adhesive is a pressure sensitive hot melt air adhesive which best provides the desirable bonding characteristics.

As described above, the ribbon is thermally-elasticizable. Preferably, it is constructed of a material that is rendered elastic when heated, and remains elastic when cooled back to room temperature. One type of material which is particularly suitable for the thermally-elasticizable ribbon 41 is a co-extruded film having an inner layer of a polyether block amide resin consisting of linear regular chains of rigid polyamide segments and flexible polyether segments, such as is produced from the commercially-available PEBAX (trademark) resins sold by ATO Chem, and outer layers of ethylene/vinyl acetate copolymer. This material is described in the copending application, attorney docket No. 6525 referred to above and can be stretched by machine direction stretching or compression rolling to create potential elastic energy which is recovered when the material is heated to its activation temperature, and remains elastic when cooled to room temperature. Thus, when heated to a temperature range of about 125° F. to 230° F., and preferably in the range of about 180° F. to 200° F., its "activation" temperature, the ribbon is rendered elastic and retains its elasticity when cooled back to room temperature.

The adhesive used to secure the ribbon 41 to the diaper 21 is preferably a hot melt pressure sensitive adhesive. These adhesives include synthetic rubber based adhesives which are particularly useful because of their elastomeric properties. Such adhesives, when used to attach a heat shrinkable ribbon to a disposable diaper, should have the following adhesive bulk properties:

Cohesive Strength—from about 10 psi to about 40 psi at 75° F. and 100% elongation Melt Viscosity—from about 20,000 centipoise (CP) to about 60,000 CP at 350° F.

Ring and Ball Softening Point—from about 190° F. to about 250° F.

Color—from about 1 to about 5 Gardner color

Pressure Sensitive Polyken Tack—from about 400 grams force to about 2000 grams force on a PET substrate Such adhesives should also have the following bondability attributes:

90° Peel Adhesion—from about 200 grams force to about 1500 grams force on a polyethylene film Static Shear Resistance—not more than 10% movement (creep) in 6 hours between PEBAX/adhesive under 500 grams load when applied to a one-half inch width polyethylene film and tested at 130° F.

Among the advantages of this type of adhesive is that it will bond substantially instantly to the strip material which is important to the high speed production rates discussed above.

The following examples identify suitable hot melt adhesives which possess the above adhesive bulk properties and bondability attributes.

EXAMPLE I

| COMPONENT | IDENTITY | COPOLYMER RATIO | TYPICAL RANGE | PREFERRED RANGE |
|---|---|---|---|---|
| Base Polymer | Co-Styrene(A)/ Butadiene(B)/ Styrene(A) (Linear Triblock) | 28%(A)/ 72%(B) | 15%–60% | 25%–45% |
| Tackifier Resin | Glycerol or Penta Erythritol Ester of Hydrogenated Rosin | | 40%–85% | 55%–75% |

EXAMPLE II

| COMPONENT | IDENTITY | COPOLYMER RATIO | TYPICAL RANGE | PREFERRED RANGE |
|---|---|---|---|---|
| Base Polymer | Co-Styrene(A)/ Isoprene(B)/ Styrene(A) (Linear Triblock 85%) | 14%(A)/ 86% | 15%–60% | 35%–55% |
| | Co-Styrene(A)/ Isoprene(B) (Linear Diblock, 15%) | 14%(A)/ 86%(B) | | |
| Tackifier Resin | 60% Piperylene 10% Isoprene 5% Cyclopentadiene 15% 2-Methyl Butene 10% Dimer (Blend) | | 40%–85% | 45%–65% |

EXAMPLE III

| COMPONENT | IDENTITY | COPOLYMER RATIO | TYPICAL RANGE | PREFERRED RANGE |
|---|---|---|---|---|
| Base Polymer | Co-Styrene(A)/ Isoprene(B) (Radical Block Copolymer) | 15%(A)/ 85%(B) | 15%–60% | 40%–60% |
| Tackifier Resin No. 1 | Hydrogenated Hydrocarbons | | 20%–80% | 30%–50% |
| Tackifier Resin No. 2 | Poly Alpha-Methyl Styrene | | 5%–50% | 7.5%–12.5% |

EXAMPLE IV

| COMPONENT | IDENTITY | COPOLYMER RATIO | TYPICAL RANGE | PREFERRED RANGE |
|---|---|---|---|---|
| Base Polymer | Co-Styrene(A)/ Isoprene(B)/ Styrene(A) (Linear Triblock) | 21.5%(A)/ 78.5%(B) | 15%–60% | 25%–45% |
| Tackifier Resin No. 1 | Polypiperylene | 20%–80% Blend | 20%–80% | 30%–50% |
| | Poly-2-Methyl-butene (Blend) | 20%–80% Blend | | |
| Tackifier Resin No. 2 | Co-Alpha-Methylstyrene/ Vinyltoluene | | 5%–50% | 15%–35% |
| Antioxidant No. 1 | 2-(2'-Hydroxy-5'-Methylphenyl) Benzotriazole | | | 0.1%–1.0% |
| Antioxidant No. 2 | Tetrakis [Methylene 3-(3',5'-Di-T-Butyl-4'-Hydroxyphenyl) Proprionate] Methane | | | 0.1%–1.0% |

EXAMPLE V

| COMPONENT | IDENTITY | COPOLYMER RATIO | TYPICAL RANGE | PREFERRED RANGE |
|---|---|---|---|---|
| Base Polymer No. 1 | Co-Styrene(A)/ Isoprene(B)/ Styrene(A) (Linear Triblock) | 14%(A)/ 86%(B) | 7.5%–30% | 15%–25% |
| | Co-Styrene(A)/ Isoprene(B) (Linear Diblock, 45%) | 14%(A)/ 86%(B) | | |
| Base Polymer No. 2 | Co-Styrene(A)/ Butadiene(B)/ Styrene(A) (Linear Triblock) | | 7.5%–30% | 15%–25% |
| Tackifier Resin No. 1 | Polydipentene | | 20%–42.5% | 25%–35% |
| Tackifier Resin No. 2 | Pentaerthritol Ester of Tall Oil Rosin | | 20%–42.5% | 25%–35% |

EXAMPLE VI

| COMPONENT | IDENTITY | COPOLYMER RATIO | TYPICAL RANGE | PREFERRED RANGE |
|---|---|---|---|---|
| Base Polymer | Co-Styrene(A)/ Butadiene(B) (Radial Triblock) | 21%(A)/ 79%(B) | 15%–60% | 30%–50% |
| Tackifier Resin | Poly Beta-Pinene | | 40%–85% | 50%–70% |

Hot melt adhesives of this type are heated and extruded at a temperature of from about 280° F. to about 375° F. It is apparent that the adhesive must be cooled to a temperature of less than 150° F. and preferably below about 125° F. before it can be applied to the ribbon 41. If not, the hot adhesive might prematurely activate the heat shrinkable material and generate process problems. However, the adhesive must remain sufficiently hot (from about 100° F. to about 120° F.) so that it will conform to the material of the ribbon and bond thereto, and so that the bonded ribbon and adhesive can thereafter be secured to the article, e.g., to the diaper.

(b) Method Description

Figure 5:
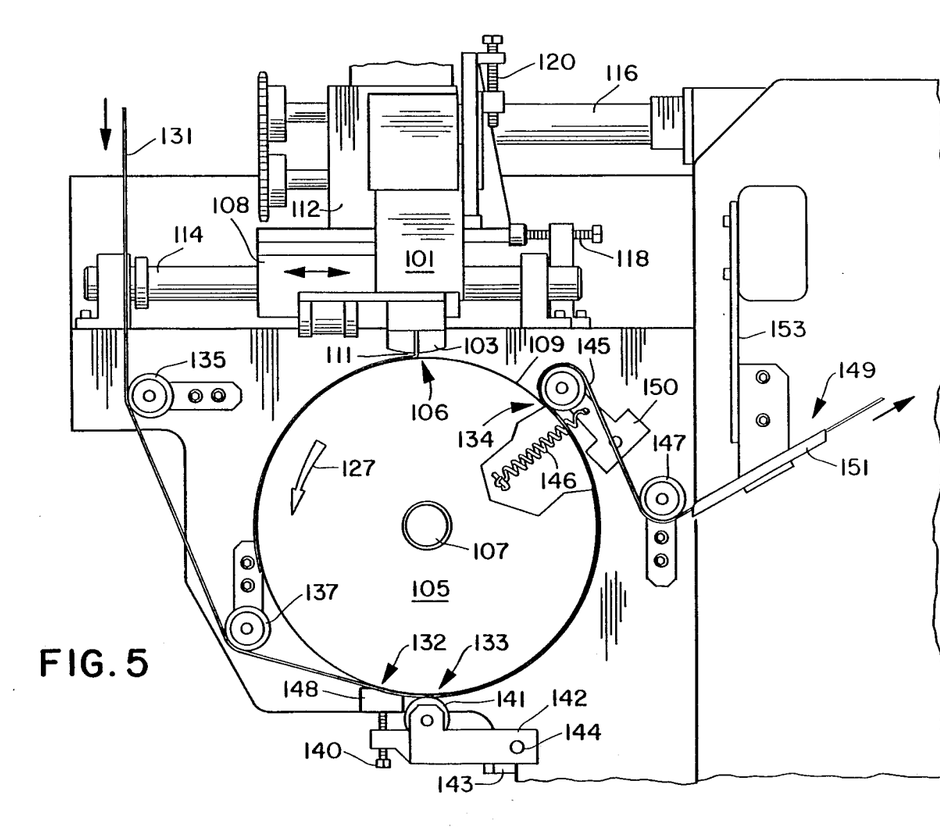
FIG. 5 is a side elevational view of a portion of an apparatus for practice of the method of this invention.
Figures 6, 7:
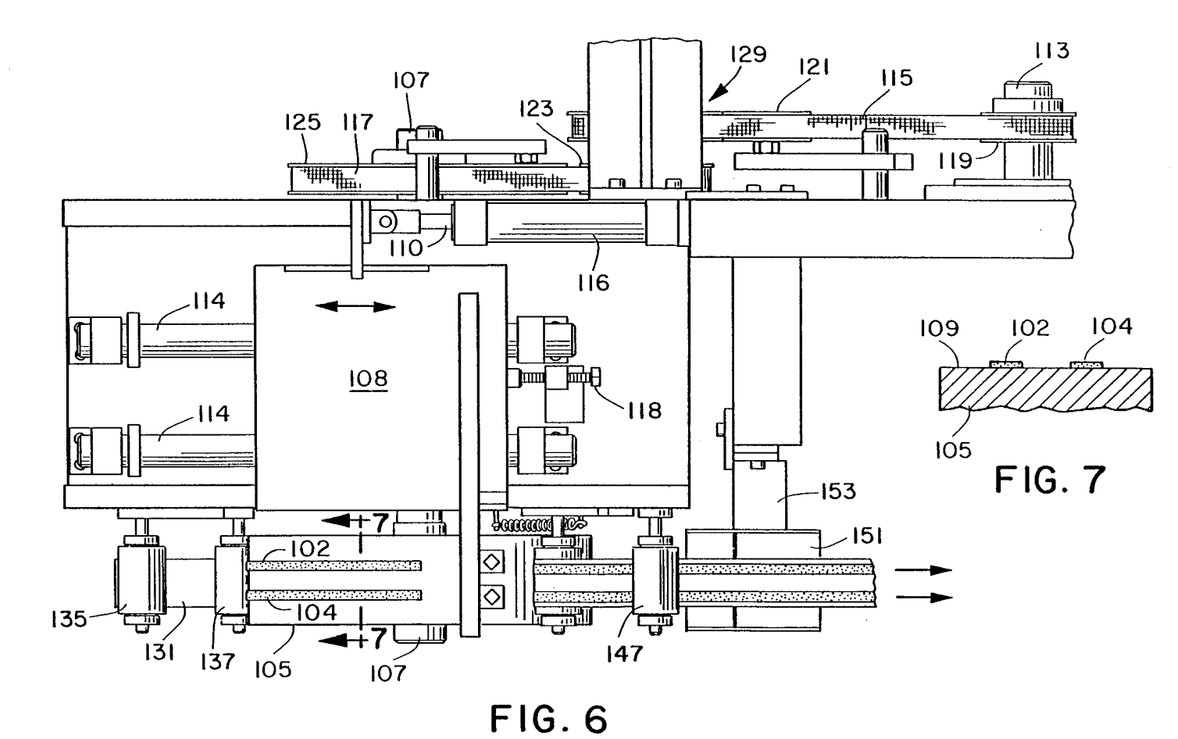
FIG. 6 is a top plan view of the apparatus of FIG. 5.
FIG. 7 is an enlarged sectional view of a portion of FIG. 6 taken along the line 7—7 thereof.

FIGS. 5–7 illustrate the application of hot melt adhesive to a heat sensitive web in accordance with the method of the invention.

Adhesive, after being heated, is extruded and deposited in at least one, and preferably two, continuous beads 102, 104 on a surface 109 of a cooled transfer mechanism rotatable chill roll 105 after a first station 106. The chill roll 105 is cooled to a temperature somewhat lower than the heated adhesive and is caused to rotate in a counterclockwise direction, as seen in FIG. 5 so that the adhesive beads 102, 104 gradually cool as they move away from station 106. Cooling of the chill roll may be effected by any suitable medium such as refrigerant, water, air, etc.

Importantly, the adhesive beads 102, 104 are of a cross-section so that cooling occurs substantially uniformly across their width. Ideally, the roll surface 109 is flat and the beads 102, 104 also are flat and generally rectangular in cross section, as shown in FIG. 7, rather than round. It will be understood that some variation in the shapes of the roll surface and the cross-section of the bead(s) may occur and may even be desirable. Nevertheless, the shape of the bead(s) must be such that when moved along with the cooled transfer mechanism (the roll 105), the adhesive beads cool substantially uniformly across their width, as described below.

A substantially continuous web 131 of heat sensitive material is brought into contact with the adhesive beads at a second station 132 downstream of the first station 106. The temperature, diameter and rotational speed of the chill roll 105, the dimensions of the beads 102, 104, and the positioning of the second station 132 relative to the first station is such that the adhesive beads 102, 104 will have cooled to a temperature below the critical temperature for the web 131. In the case of a heat shrinkable material described above, the critical temperature is the activation temperature at which the material shrinks, or from about 125° F. to about 230° F. In that case, the adhesive beads 102, 104 should be less than 125° F. at station 132, and preferably should be from about 100° F. to about 120° F.

In accordance with the invention, the web 131 is pressed into intimate contact with the adhesive beads 102, 104. "Pressure" engagement may occur substantially simultaneously with "contact" engagement. However, it has been found advantageous to apply pressure to press the web 131 into intimate contact with the adhesive at a station 133 which is downstream of the initial contact point (station 132) because it allows the web 131 to stick to the adhesive before pressure is applied. This minimizes or eliminates lateral movement of the web 131 which otherwise may occur if pressure is applied at the initial contact point. The temperature of the adhesive at pressure station 132 should be hot enough so that the adhesive conforms to the web to effect strong bonding.

The "married" web and adhesive continue on the surface of the chill roll 105 and are stripped from the roll at a station 134. The web and adhesive continue to bond firmly together during this time while the adhesive is cooled further making the stripping step more easily achieved. Preferably, the web and adhesive are stripped from the chill roll by wrapping around a peel-off roll 145 at least about 90° and preferably about 180°.

The married web and adhesive then conveniently move to a cutting station 149 where the web is cut into the desired lengths which then can be pressure applied immediately, for example, as ribbons 41 to the disposable diapers 21. Alternatively, it will be understood that the web and adhesive could first move to another processing station before being cut.

In the method of this invention, the adhesive is heated and extruded through an exit nozzle onto the surface of the cooling transfer mechanism, here, the chill roll 105. It has been found that by providing a controlled gap between the exit nozzle and the chill roll surface, and by shaping the exit nozzle profile properly to the profile of the roll surface, adhesive is deposited as a bead having a cross-section which promotes substantially uniform cooling of the bead across its width. In the most preferential version, the roll surface 109 is flat and the bead(s), 102, 104 also are relatively flat and have a generally rectangular cross-section as opposed to a round cross-section. The relatively flat, generally rectangular cross-sectional bead is desirable in that it promotes uniform cooling of the adhesive. Contrasted with this is a round cross-sectional adhesive bead wherein the outer shell of the bead cools quickly while the inside remains relatively hot. In that case, when the bead is squashed by pressure engagement with the web, sufficient heat may be given off to damage or activate the heat sensitive web material. Cooling a rounded bead sufficiently to prevent this adverse reaction likely will cool the adhesive to a point where bonding is less effective.

It will be understood that it is important that the temperature at the exit nozzle 103 reach the desired operating level, i.e., from about 280° F. to about 375° F. in the case of the preferred adhesive, as quickly as possible and that this temperature be maintained even in the event of temporary interruption or shutdown. To this end, the method of this invention provides that the exit nozzle 103 is indexed away from the cooled transfer mechanism (chill roll 105) when the inventive method is not being performed and during temporary interruption or shutdown. This prevents the chill roll 105 from delaying the exit nozzle 103 from becoming heated during start-up, and prevents undesired cooling of the nozzle 103 during temporary shutdown. In addition, and in accordance with the invention, the exit nozzle is indexed toward the chill roll 105 when it reaches the desired temperature to commence the inventive method.

The temperatures achieved during the method of the invention will vary according to the materials used. In the case of the preferred form of synthetic rubber based hot melt, pressure sensitive adhesive described above, which is a preferred adhesive used with a heat sensitive material constructed of a co-extruded film having an inner layer produced from PEBAX (trademark) and outer layers of ethylene/vinyl acetate copolymer, the adhesive is heated and extruded and deposited on the chill roll at a temperature of from about 280° F. to about 375° F. The chill roll 105 is cooled by refrigeration to a temperature of from about 30° F. to about 65° F. to cool the adhesive ribbon to a temperature of less than 125° F. at station 132. The bonded adhesive and web are stripped from the chill roll at station 134 with the adhesive at a temperature of from about 100° F. to about 120° F.

It will be understood that different adhesives may require different temperatures and thicknesses of the deposited ribbon. It has been found that the exit nozzle should be disposed substantially perpendicular to the chill roll surface, and that the thickness of the deposited bead should be substantially equal to the gap between the nozzle and roll surface. For the preferred adhesive and ribbon materials described above, adhesive beads of about 0.010 inches thick have been found preferable. It is possible to use thinner beads of adhesive, particularly with adhesives having higher cohesive strengths.

(c) Apparatus Description

FIGS. 5–7 also depict an apparatus of this invention which is particularly useful for practicing the method described in part (b).

Referring to FIGS. 5 and 6, the apparatus comprises means for heating and extruding an adhesive, the extruding means having an exit nozzle, a cooling transfer mechanism disposed adjacent to and spaced from the exit nozzle by a gap for receiving a continuous bead of the adhesive deposited on the roll at a first station, the bead having a cross-section operable to promote substantially uniform cooling across its width. As embodied herein and shown in FIG. 5, an extruder, generally indicated at 101, is of conventional construction and includes a metering pump and heated passages (not shown), and is provided with an exit nozzle 103 through which the heated adhesive is extruded, as will be understood by those skilled in the art. In the case of the hot melt pressure sensitive adhesive described herein, the adhesive is heated in the extruder to a temperature of from about 280° F. to about 375° F. The exit nozzle 103 includes one or more openings through which the hot melt adhesive is delivered. In the case where two parallel adhesive beads are desired, the nozzle 103 has two openings.

The chill roll 105 is rotatably supported by a shaft 107 and has a generally cylindrical surface 109 adjacent the exit nozzle 103 but spaced therefrom by a gap 111. The profile of roll surface 109 is generally complimentary to the profile of the exit nozzle, and preferably both are relatively flat. A motor-driven shaft 113 is connected through a series of belts 115, 117, and pulleys 119, 121, 123, 125 to the roll shaft 107. A clutch and brake mechanism 129 is provided for the chill roll 105.

The direction of rotation of the depicted chill roll 105 is, as shown by the arrow 127 in FIG. 5, in a counter-clockwise direction. During rotation of the chill roll 105, hot melt adhesive is extruded and deposited in at least one and preferably two continuous beads 102, 104 on the surface 109 of roll 105 at station 106. As a result of the complimentary flat profiles of the exit nozzle 103 and roll surface 109, the adhesive beads 102, 104 are flat and generally rectangular in cross section, and the thickness of the beads is substantially equal to the dimension of gap 111 as shown in FIG. 5. Relatively flat, generally rectangular beads which are produced by the gapped and flat profiled exit nozzle and roll surface are preferable because cooling is substantially uniform across their width. However, it will be understood that a perfectly flat and rectangular shape is likely not to occur. Furthermore, it may be desirable to form the beads of another cross-section. Importantly, the bead(s) should have a cross-sectional configuration which promotes substantially uniform cooling across their width for proper bonding to the heat sensitive web with minimum adverse effects. As will be understood by those skilled in the art, the chill roll 105 is cooled by conventional refrigeration or other suitable cooling medium so that as the adhesive travels on the surface of the rotating chill roll, its temperature cools.

In accordance with the invention, the exit nozzle of the extruder is movable away from the chill roll during start-up of the mechanism to allow the exit nozzle to reach its operating temperature as quickly as possible. In addition, the exit nozzle moves away from the chill roll in the event of temporary shutdown to prevent adhesive in the extruder from cooling.

As embodied herein and shown in FIGS. 5 and 6, the extruder 101 is mounted on a base plate 108 fixed to a slide bracket 112 which is slidably guided on bars 114. A pneumatic motor 116 includes a piston rod 110 connected to the base plate 108 and is operable to shift the extruder 101 to the left or right, as seen in FIG. 5. Adjustment screw 118 provides an adjustable stop for lateral movement of the extruder 101 toward the right, as shown in FIG. 5, and adjustment screw 120 adjusts the extruder toward and away from the chill roll 105 to vary the size of gap 111.

In start-up, the motor 116 is set so that the extruder 101 is positioned toward the left from the position shown in FIG. 5 and the exit nozzle 103 moved away from the chill roll surface 109. The extruder 101 is actuated and adhesive therein is heated and extruded through the exit nozzle 103 causing it to heat rapidly. When the nozzle reaches its operating temperature, which in the case of the preferred adhesive described above is from about 280° F. to about 375° F., the motor 116 is operated to move the extruder 101 back toward the right and to the position seen in FIG. 5. Movement terminates when the base plate 108 engages screw 118. The exit nozzle 103 thus is properly positioned relative to the chill roll surface 109 for deposition of adhesive bead(s) thereon.

In the event of temporary shutdown, the motor 116 is operated to move the extruder toward the left, as seen in FIG. 5, and to position the exit nozzle 103 away from the chill roll. This prevents adhesive in the extruder from becoming adversely cooled during shutdown as would otherwise occur. Those skilled in the art will understand that suitable controls can be provided to render operation of the motor 116 described above automatic.

In accordance with the invention, means is provided for feeding a web of heat sensitive material into contact with the cooling transfer mechanism surface and the adhesive bead, and means is provided for pressing the web into contact with the adhesive and chill roll. As embodied herein, a substantially continuous web of heat sensitive material 131 from a suitable source (not shown) is brought into contact with the chill roll surface 109 and the adhesive beads 102, 104 at a second station 132 which is nearly 180° downstream from the first station 106. As shown in FIG. 5, the heat sensitive material 131 moves over idler rollers 135, 137 and into contact with the adhesive beads 102, 104 at the station 132 and joins or marries with the adhesive at this point. The chill roll 105 as described above, is cooled by refrigeration so that its temperature is somewhat less than the temperature of the hot melt adhesive and causes the adhesive to cool to the desired temperature by the time it reaches station 132. The web 131 and the adhesive stick together at this point which prevents the web 131 from moving laterally relative to the roll 105.

As further embodied herein, a nip roller 141 is mounted on an arm 142 pivoted about a pin 144. The roller 141 is biased toward the chill roll by suitable means such as a pneumatic pressure device 143. The nip roller 141 engages the chill roll surface 109 at third station 133 and presses the web 131 and adhesive into intimate contact, causing the adhesive to spread and conform to the web material. The engagement pressure is limited and adjusted by a screw 146 which engages a stationary pad 148. The third or pressure station 133 is downstream of the second or contact station 132 where the web 131 first contacts the adhesive so that the web and adhesive will have become stuck before reaching station 133. This helps prevent lateral movement of the web 131 at station 133.

In accordance with the invention, means is provided for stripping the bonded web and adhesive from the chill roll at a fourth station downstream of the third station. As embodied herein, a peel-off roller 145 is positioned downstream of the nip roller 141 and station 133 and engages the chill roll 105 at a fourth station 134. The roller 145 is carried by a pivoted arm 150 and is biased into engagement with chill roll 105 by a tension spring 146 to insure that roller 145 rotates at the same speed as chill roll 105. The position of the roller 145 and station 134 is such that the adhesive and web will have had time to become firmly bonded. Importantly, the bonded web and adhesive are stripped from chill roll 105 by wrapping around the peel-off roll 145 at least 90° and preferably about 180°, as shown in FIG. 5. It has been found that this facilitates highly efficient removal of the web and bonded adhesive from the chill roll 105.

As described above, the method and apparatus of the present invention find particular use in forming heat shrinkable ribbons for attachment to disposable garments such as diapers. In that case, the web and bonded adhesive are delivered to a cut-off station 149, although it will be understood that there can be other intermediate processing stations, if desired. As shown in FIG. 5, the web and bonded adhesive, after leaving roller 145, is fed under an idler roller 147 to the cut-off station 149 which can include a stationary platen 151 and a motor driven reciprocating knife 153. In this manner, the web and adhesive can be cut into the desired strip lengths, such as the illustrated ribbons 41 described above. Immediately thereafter, the ribbons can be applied by pressure to the diapers 21.

In the case of the preferred synthetic rubber based hot melt, pressure sensitive adhesive and heat shrinkable web material described herein, the working surface portion of chill roll 105 preferably is constructed with a coating of ceramic impregnated with polytetrafluoroethylene. Compared to other type roll surfaces such as, for example, silicone rubber, the impregnated ceramic surface provides excellent wear resistance and low adhesion.

Nip roller 141 and stripping roller 145 preferably are of steel cored construction having working surfaces of silicone rubber.

(d) Operational Conditions

It has been determined that the hot melt adhesive described above should be heated to a temperature from about 280° F. to a temperature of about 375° F. When this occurs, the extruder is moved into position with the exit nozzle 103 adjacent roll surface 109 and adhesive is extruded and deposited on the chill roll in generally flat substantially rectangular beads about 0.010 inches thick, although temperatures and bead thicknesses outside this range can be used depending upon the particular adhesive employed. Notably, thinner beads can be employed when using adhesives having higher cohesive strengths. In general, temperatures of this magnitude are unsuitable for direct application of the adhesive to the pressure sensitive web 131, particularly when the web is one which is constructed of a heat shrinkable material. In this invention, the temperature of the adhesive beads is brought substantially uniformly to a point below that where an adverse effect would be produced on the heat sensitive web material 131 before the web and adhesive join together. Thus, in the particular example given, the temperature of the adhesive is lowered as it travels along the chill roll 105 to below 125° F., preferably from about 100° F. to about 120° F. In this manner, no adverse effect is produced on the web when the adhesive and web join at station 132 and yet the adhesive is hot enough to conform and bond to the web. Thereafter, the nip roll 141 presses the web 131 and adhesive into intimate contact.

Rotation of the chill roll 105 with the intimately-engaged web 131 and adhesive continues causing the temperature of the adhesive to lower even further and the web and adhesive to securely bond together. By the time the adhesive and web reach the peel-off roll 145 at stripping station 134, the temperature of the adhesive will be from about 100° F. to about 120° F.

The bonded web and adhesive are stripped from the chill roll 105 by wrapping around the peel-off roller 145 at least about 90° and preferably about 180°, as shown in FIG. 5. This very efficiently and effectively removes the web 131 and bonded adhesive when then can be delivered to the cut-off station 149.

In the event of temporary shutdown, the extruder 101 is moved away from chill roll 105 to avoid undesired cooling of adhesive in the extruder.

By the foregoing, there has been disclosed a method and apparatus for applying a hot melt pressure sensitive adhesive to a web of heat sensitive material, and a resulting product calculated to fulfill the inventive objects set forth and inherent herein. While preferred embodiments of the invention are described and depicted herein, it will be apparent to those skilled in the art that various additions, substitutions, modifications and omissions can be made to the present invention without departing from the scope or spirit of the invention. Thus, it is intended that the present invention cover those additions, substitutions, modifications and omissions provided they come within the scope of the appended claims and their equivalents.

We claim:

1. A garment article, comprising:
a body of gatherable material; and
an elasticized tape connected to a selected portion of said gatherable material, said tape including,
a thermally-elasticizable ribbon having an activation temperature at which said ribbon shrinks to an elastic state, and
a layer of hot melt, pressure-sensitive adhesive disposed on a surface of said ribbon to connect said ribbon to said gatherable material, said hot melt adhesive composed of a base polymer and a tackifier resin and having a hot melt extrusion temperature which is higher than said activation temperature of said ribbon, said adhesive sufficiently conformed and bonded to said ribbon so that said ribbon is secured to said gatherable material, and said ribbon activated by the application of heat to shir said gatherable material.

2. A garment as recited in claim 1, wherein said layer of hot melt adhesive is in the form of one or more spaced parallel lines extending longitudinally of the ribbon.

3. A garment as recited in claim 1, wherein said hot melt adhesive is disposed in a continuous layer on the surface of said ribbon.

4. A garment as recited in claim 1, wherein said ribbon has an activation temperature within the range of about 180°-200° F.

5. A garment as recited in claim 1, wherein said ribbon comprises a co-extruded film having an inner layer of a polyether block amide resin consisting of linear regular chains of rigid polyamide segments and flexible polyether segments, and at least one outer layer of ethylene/vinyl acetate copolymer.

6. A garment article, comprising:
a body of gatherable material; and
an elasticized tape connected to a selected portion of said gatherable material, said tape including,
a thermally-elasticized ribbon having an activation temperature within the range of about 125°-230° F. at which temperature said ribbon shrinks to an elastic state, and
a layer of hot melt, pressure-sensitive adhesive disposed on a surface of said ribbon to connect said ribbon to said gatherable material, said adhesive composed of a base polymer and a tackifier resin and having a hot melt extrusion temperature which is higher than said ribbon activation temperature, said adhesive sufficiently conformed and bonded to said ribbon so that said ribbon is secured to said gatherable material, and said ribbon activated by the application of heat to shir said gatherable material.

7. A garment as recited in claim 6, wherein said layer of hot melt adhesive is in the form of one or more spaced parallel lines extending longitudinally of the ribbon.

8. A garment as recited in claim 6, wherein said hot melt adhesive is disposed in a continuous layer on the surface of said ribbon.

9. A garment as recited in claim 6, wherein said ribbon has an activation temperature within the range of about 180°-200° F.

10. A garment as recited in claim 6, wherein said ribbon comprises a co-extruded film having an inner layer of a polyether block amide resin consisting of linear regular chains of rigid polyamide segments and flexible polyether segments, and at least one outer layer of ethylene/vinyl acetate copolymer.

11. A garment article, comprising:
a body of gatherable material; and
an elasticized tape connected to a selected portion of said gatherable material, said tape including,
a thermally-elasticizable ribbon having an activation temperature at which said ribbon shrinks to an elastic state, and
a layer of hot melt, pressure-sensitive adhesive disposed on a surface of said ribbon to connect said ribbon to said gatherable material, said adhesive composed of a base polymer and a tackifier resin and having a hot melt extrusion temperature which is higher than said ribbon activation temperature and is within the range of about 280°-375° F., said adhesive sufficiently conformed and bonded to said ribbon so that said ribbon is secured to said gatherable material, and said ribbon activated by the application of heat to shir said gatherable material.

12. A garment as recited in claim 11, wherein said layer of hot melt adhesive is in the form of one or more spaced parallel lines extending longitudinally of the ribbon.

13. A garment as recited in claim 11, wherein said hot melt adhesive is disposed in a continuous layer on the surface of said ribbon.

14. A garment as recited in claim 11, wherein said ribbon has an activation temperature within the range of about 125°–230° F.

15. A garment as recited in claim 11, wherein said ribbon has an activation temperature within the range of about 180°–200° F.

16. A garment as recited in claim 11, wherein said ribbon comprises a co-extruded film having an inner layer of a polyether block amide resin consisting of linear regular chains of rigid polyamide segments and flexible polyether segments, and at least one outer layer of ethylene/vinyl acetate copolymer.

* * * * *